(12) United States Patent
Liu et al.

(10) Patent No.: US 12,356,537 B2
(45) Date of Patent: Jul. 8, 2025

(54) NEUTRON CAPTURE THERAPY SYSTEM

(71) Applicant: NEUBORON THERAPY SYSTEM LTD., Fujian (CN)

(72) Inventors: Yuan-hao Liu, Fujian (CN); Chun-ting Lin, Fujian (CN)

(73) Assignee: NEUBORON THERAPY SYSTEM LTD., Fujian (CN)

( * ) Notice: Subject to any disclaimer, the term of this patent is extended or adjusted under 35 U.S.C. 154(b) by 0 days.

(21) Appl. No.: 18/802,160

(22) Filed: Aug. 13, 2024

(65) Prior Publication Data

US 2024/0431014 A1    Dec. 26, 2024

Related U.S. Application Data

(63) Continuation of application No. 18/413,207, filed on Jan. 16, 2024, now Pat. No. 12,238,850, which is a
(Continued)

(30) Foreign Application Priority Data

Jul. 16, 2021    (CN) .......................... 202110807267.1

(51) Int. Cl.
  *H05H 3/06*    (2006.01)
  *A61N 5/10*    (2006.01)
  (Continued)

(52) U.S. Cl.
  CPC ............. *H05H 3/06* (2013.01); *A61N 5/1077* (2013.01); *C23C 14/165* (2013.01); *C23C 14/34* (2013.01);
  (Continued)

(58) Field of Classification Search
  CPC .... H05H 3/06; H05H 2277/11; A61N 5/1077; A61N 2005/109; C23C 14/165;
  (Continued)

(56) References Cited

U.S. PATENT DOCUMENTS 4,298,804 A    11/1981    Colditz
6,130,926 A    10/2000    Amini
(Continued)

FOREIGN PATENT DOCUMENTS

CN    106605140 A    4/2017
CN    108093552 A    5/2018
(Continued)

OTHER PUBLICATIONS

Satoshi Nakamura et al., "Neutron flux evaluation model provided in the accelerator-based boron neutron 1 capture therapy system employing a solid-state lithium target", Scientific Reports, Nov. 1, pp. 1-13, 2021.

*Primary Examiner* — James R Greece
*Assistant Examiner* — Jose M Diaz
(74) *Attorney, Agent, or Firm* — troutman pepper locke; Tim Tingkang Xia, Esq.

(57) ABSTRACT

A neutron capture therapy system and a target material for a particle beam generation apparatus, the heat dissipation performance of a target material might be improved. A neutron capture therapy system includes a neutron generation apparatus and a beam shaping body, the neutron generation apparatus includes an accelerator and a target material, and a charged particle beam generated by means of acceleration of the accelerator acts with the target material to generate a neutron beam. The target material includes an active layer, an anti-foaming layer, a heat dissipation layer and a heat conduction layer, the active layer acts with a charged particle beam to generate a neutron beam; the anti-foaming layer suppresses foaming caused by the charged particle beam; the heat dissipation layer directly and rapidly conducts to the heat conduction layer, heat deposited on the active layer, and discharges by means of a cooling medium.

19 Claims, 9 Drawing Sheets

Related U.S. Application Data continuation of application No. PCT/CN2022/105408, filed on Jul. 13, 2022.

(51) Int. Cl.
*C23C 14/16* (2006.01)
*C23C 14/34* (2006.01)
*C23C 16/40* (2006.01)
*C23C 16/455* (2006.01)
*C23C 28/00* (2006.01)

(52) U.S. Cl.
CPC ...... C23C 16/403 (2013.01); C23C 16/45555 (2013.01); C23C 28/322 (2013.01); C23C 28/345 (2013.01); *A61N 2005/109* (2013.01); *H05H 2277/11* (2013.01)

(58) Field of Classification Search
CPC . C23C 14/34; C23C 16/403; C23C 16/45555; C23C 28/322; C23C 28/345; H01J 27/02; H01J 49/10
USPC ....................... 313/46, 42, 47, 230
See application file for complete search history.

(56) References Cited

U.S. PATENT DOCUMENTS

| | | | |
|---|---|---|---|
| 2012/0135650 A1 | 5/2012 | Servante et al. | |
| 2019/0262632 A1* | 8/2019 | Liu | H05H 6/00 |
| 2021/0076481 A1 | 3/2021 | Jauregui et al. | |

FOREIGN PATENT DOCUMENTS

| | | |
|---|---|---|
| CN | 108236760 A | 7/2018 |
| CN | 108827994 A | 11/2018 |
| CN | 109381802 A | 2/2019 |
| CN | 109464751 A | 3/2019 |
| CN | 111212510 A | 5/2020 |
| CN | 112933422 A | 6/2021 |
| EP | 1895819 A1 | 3/2008 |
| JP | 2016136499 A | 7/2016 |
| JP | 2020513885 A | 5/2020 |
| KR | 20100042841 A | 4/2010 |
| TW | 201414362 A | 4/2014 |
| TW | 201706008 A | 2/2017 |
| TW | 201824962 A | 7/2018 |
| TW | 201912199 A | 4/2019 |
| WO | 2019236537 A2 | 12/2019 |

\* cited by examiner

NEUTRON CAPTURE THERAPY SYSTEM

CROSS-REFERENCE TO RELATED PATENT APPLICATION

This application is a continuation application of U.S. patent application Ser. No. 18/413,207, filed on Jan. 16, 2024, which is a continuation application of International Application No. PCT/CN2022/105408, filed on Jul. 13, 2022, which claims priority to Chinese Patent Application No. 202110807267.1, filed on Jul. 16, 2021, the disclosures of which are hereby incorporated by reference.

TECHNICAL FIELD

The disclosure relates to a target for a radioactive ray irradiation system, and in particular to a neutron capture therapy system comprising a target for a device for generating a particle beam.

BACKGROUND

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the disclosure.

With the development of atomics, radioactive ray therapy, such as cobalt sixty, a linear accelerator, an electron beam, or the like, has become one of the major means to treat cancers. However, traditional photon or electron therapy is restricted by physical conditions of radioactive rays themselves, and thus will also harm a large number of normal tissues on a beam path while killing tumor cells. Furthermore, owing to different levels of sensitivity of tumor cells to radioactive rays, traditional radiotherapy usually has poor treatment effect on malignant tumors (for example, glioblastoma multiforme and melanoma) with radio resistance.

In order to reduce radiation injury to normal tissues around tumors, a target therapy concept in chemotherapy is applied to radioactive ray therapy. With respect to tumor cells with high radio resistance, irradiation sources with high relative biological effectiveness (RBE), such as proton therapy, heavy particle therapy, neutron capture therapy, or the like, are also developed actively now. Here neutron capture therapy combines the abovementioned two concepts, for example, boron neutron capture therapy (BNCT), provides a better cancer treatment choice than traditional radioactive rays, by aggregation of boron-containing drugs in tumor cells in combination with precise neutron beam regulation and control.

In BNCT with an accelerator, a proton beam is accelerated by the accelerator, to reach an energy sufficient to overcome Coulomb repulsive forces of atomic nucleus of a target, and generate a nuclear reaction with the target to generate neutrons. Therefore, during generation of the neutrons, the target is subjected to irradiation of the accelerated proton beam with a very high energy level, and temperature of the target increases significantly, while metal parts of the target are easy to foam, thereby affecting service life of the target.

Therefore, it needs to propose a new technical solution.

SUMMARY

According to an aspect of the disclosure, there is provided a target for a device for generating a neutron beam, the target includes an active layer, an anti-foaming layer, a heat dissipation layer and a heat conduction layer, the active layer acts with a charged particle beam to generate a neutron beam, the anti-foaming layer is located behind the active layer in an incident direction of the charged particle beam and capable of suppressing foaming induced by the charged particle beam, the heat dissipation layer transfers heat deposited in the target out, and the heat conduction layer conducts heat of the active layer to the heat dissipation layer.

Further, the heat conduction layer may be arranged between the active layer and the anti-foaming layer, and connected to the heat dissipation layer. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged; heat conduction is not substantially performed through the anti-foaming layer, and the anti-foaming layer needs to consider anti-foaming characteristics without considering thermal conductivity thereof.

Furthermore, the heat conduction layer and the heat dissipation layer may surround the anti-foaming layer, and the heat dissipation layer or the heat conduction layer may be formed with an accommodation space configured to accommodate the anti-foaming layer.

Furthermore, the accommodation space may include a bottom surface and a side wall connected to the bottom surface, and the anti-foaming layer may be provided with a top surface in contact with the bottom surface and an outer wall in contact with the side wall.

Further, material of the active layer may be Li, or a compound of Li, or an alloy of Li, and material of each of the heat dissipation layer and the heat conduction layer may be Cu, or a compound of Cu, or an alloy of Cu, and material of the anti-foaming layer may be Ta, or a compound of Ta, or an alloy of Ta.

Further, the target may have a plate shape and have a central axis perpendicular to a surface of the plate, and along a same radial direction perpendicular to the central axis, a maximum distance from the active layer to the central axis is less than a maximum distance from the anti-foaming layer to the central axis, and the maximum distance from the anti-foaming layer to the central axis is less than a maximum distance from each of the heat dissipation layer and the heat conduction layer to the central axis.

Further, the target may further include an anti-oxidation layer configured to prevent oxidation of the active layer and isolate the active layer from air, and the anti-oxidation layer, the active layer, the heat conduction layer, the anti-foaming layer and the heat dissipation layer may be sequentially arranged in the incident direction of the charged particle beam.

Furthermore, the active layer, the heat conduction layer and the anti-foaming layer may be sequentially processed onto the heat dissipation layer by way of forming films, and the anti-oxidation layer may be processed onto the active layer by way of forming a film, or the anti-oxidation layer may be a polymer film and processed onto the active layer by a film covering process.

Furthermore, the anti-oxidation layer may be made of Al or $Al_2O_3$ or polyimide, and enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam.

Furthermore, the polyimide may have a molecular structural formula as follows:

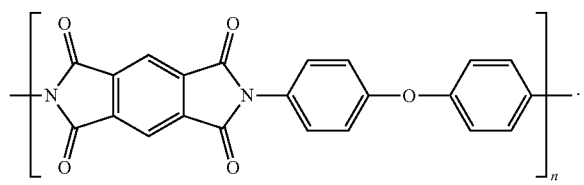

According to a second aspect of the disclosure, there is provided a target for a device for generating a particle beam, the target includes an active layer, an anti-foaming layer, a first heat dissipation layer and a second heat dissipation layer, the active layer is configured to generate the particle beam, the anti-foaming layer is capable of suppressing foaming of the active layer during generation of the particle beam, the first heat dissipation layer and the second heat dissipation layer transfer heat deposited in the target out, the anti-foaming layer is arranged between the first heat dissipation layer and the second heat dissipation layer, and the first heat dissipation layer conducts heat of the active layer to the second heat dissipation layer. Since the anti-foaming layer has poor heat dissipation performance and cannot effectively conduct heat deposited in the active layer to the heat dissipation layer, the first heat dissipation layer is arranged to directly and rapidly conduct heat deposited in the active layer to the second heat dissipation layer, the heat is discharged on the second heat dissipation layer through a cooling medium, so that temperature of the target is reduced, deformation of the target due to too high temperature is prevented, and service life of the target is prolonged; heat conduction is not substantially performed through the anti-foaming layer, and the anti-foaming layer needs to consider anti-foaming characteristics without considering thermal conductivity thereof.

Further, the first heat dissipation layer may be arranged between the active layer and the anti-foaming layer, and connected to the second heat dissipation layer, so that the first heat dissipation layer has a large area contacting with the active layer and may rapidly conduct heat to the second heat dissipation layer.

Furthermore, the first heat dissipation layer and the second heat dissipation layer may surround the anti-foaming layer, and the first heat dissipation layer or the second heat dissipation layer may be formed with an accommodation space configured to accommodate the anti-foaming layer. Heat conduction is not substantially performed through the anti-foaming layer, and the anti-foaming layer needs to consider anti-foaming characteristics without considering thermal conductivity thereof.

Furthermore, the accommodation space may include a bottom surface and a side wall connected to the bottom surface, and the anti-foaming layer may be provided with a top surface in contact with the bottom surface and an outer wall in contact with the side wall.

Further, the target may further include an anti-oxidation layer configured to prevent oxidation of the active layer, and the anti-oxidation layer, the active layer, the first heat dissipation layer, the anti-foaming layer and the second heat dissipation layer may be sequentially arranged. The anti-oxidation layer enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam.

Furthermore, the active layer, the first heat dissipation layer and the anti-foaming layer may be sequentially processed onto the second heat dissipation layer by way of forming films, and the anti-oxidation layer may be processed onto the active layer by way of forming a film, or the anti-oxidation layer may be a polymer film and processed onto the active layer by a film covering process.

Furthermore, the target may have a plate shape and have a central axis perpendicular to a surface of the plate, and along a same radial direction perpendicular to the central axis, a maximum distance from the active layer to the central axis is less than a maximum distance from each of the anti-foaming layer and the anti-oxidation layer to the central axis, and the maximum distance from the anti-foaming layer to the central axis is less than a maximum distance from each of the first heat dissipation layer and the second heat dissipation layer to the central axis.

Furthermore, material of the active layer may be Li, or a compound of Li, or an alloy of Li, and material of each of the first heat dissipation layer and the second heat dissipation layer may be Cu, or a compound of Cu, or an alloy of Cu, and material of the anti-foaming layer may be Ta, or a compound of Ta, or an alloy of Ta, and material of the anti-oxidation layer may be Al or $Al_2O_3$ or polyimide.

Furthermore, the polyimide may have a molecular structural formula as follows:

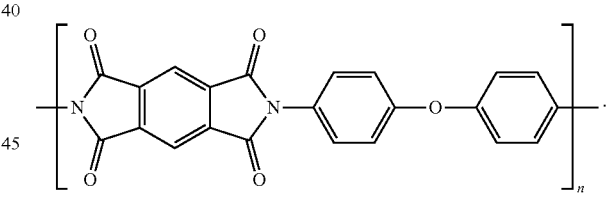

According to a third aspect of the disclosure, there is provided a target for a device for generating a particle beam, the target includes an active layer, an anti-foaming layer, a first heat dissipation layer and a second heat dissipation layer, the active layer is configured to generate the particle beam, the anti-foaming layer is capable of suppressing foaming of the active layer during generation of the particle beam, the first heat dissipation layer and the second heat dissipation layer transfer heat deposited in the target out and are connected to each other, the first heat dissipation layer is arranged between the active layer and the anti-foaming layer. Since the anti-foaming layer has poor heat dissipation performance and cannot effectively conduct heat deposited in the active layer to the heat dissipation layer, the first heat dissipation layer is arranged to directly and rapidly conduct heat deposited in the active layer to the second heat dissipation layer, the heat is discharged on the second heat dissipation layer through a cooling medium, so that temperature of the target is reduced, deformation of the target due to too high temperature is prevented, and service life of the target is prolonged; the first heat dissipation layer has a large area contacting with the active layer and may rapidly conduct heat to the second heat dissipation layer.

Further, the first heat dissipation layer and the second heat dissipation layer may surround the anti-foaming layer, and the first heat dissipation layer or the second heat dissipation layer may be formed with an accommodation space configured to accommodate the anti-foaming layer. Heat conduction is not substantially performed through the anti-foaming layer, and the anti-foaming layer needs to consider anti-foaming characteristics without considering thermal conductivity thereof.

Further, the target may further include an anti-oxidation layer configured to prevent oxidation of the active layer, and the anti-oxidation layer, the active layer, the first heat dissipation layer, the anti-foaming layer and the second heat dissipation layer may be sequentially arranged. The anti-oxidation layer enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam.

Furthermore, the active layer, the first heat dissipation layer and the anti-foaming layer may be sequentially processed onto the second heat dissipation layer by way of forming films, and the anti-oxidation layer may be processed onto the active layer by way of forming a film, or the anti-oxidation layer may be a polymer film and processed onto the active layer by a film covering process.

Furthermore, the target may have a plate shape and have a central axis perpendicular to a surface of the plate, and along a same radial direction perpendicular to the central axis, a maximum distance from the active layer to the central axis is less than a maximum distance from each of the anti-foaming layer and the anti-oxidation layer to the central axis, and the maximum distance from the anti-foaming layer to the central axis is less than a maximum distance from each of the first heat dissipation layer and the second heat dissipation layer to the central axis.

Furthermore, material of the active layer may be Li, or a compound of Li, or an alloy of Li, and material of each of the first heat dissipation layer and the second heat dissipation layer may be Cu, or a compound of Cu, or an alloy of Cu, and material of the anti-foaming layer may be Ta, or a compound of Ta, or an alloy of Ta, and material of the anti-oxidation layer may be Al or $Al_2O_3$ or polyimide.

Furthermore, the polyimide may have a molecular structural formula as follows:

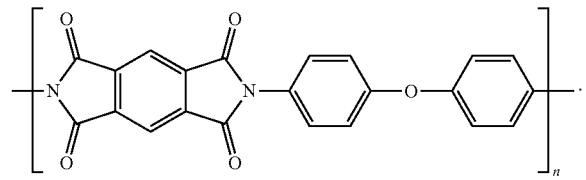

According to a fourth aspect of the disclosure, there is provided a target for a device for generating a particle beam, the target includes an anti-oxidation layer, an active layer, an anti-foaming layer and a heat dissipation layer, the active layer acts with an incident charged particle beam to generate a neutron beam, the anti-foaming layer is capable of suppressing foaming of the active layer during generation of the particle beam, the anti-oxidation layer is a polymer film and isolates the active layer from air, to enable the target to be exposed to the air without technical storage, the anti-oxidation layer is very convenient especially when the target is installed and replaced, and the anti-oxidation layer may also prevent by-product of the active layer from overflowing the target.

Further, material of the polymer film may be polyimide with a molecular structural formula as follows:

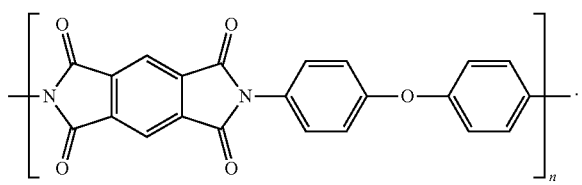

Further, the anti-oxidation layer may be processed onto the active layer by a film covering process. Furthermore, the anti-oxidation layer may have a thickness greater than 5 nm.

Further, the target may further include a heat conduction layer. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged; the anti-foaming layer may be arranged between the heat conduction layer and the heat dissipation layer, the heat conduction layer may be connected to the heat dissipation layer, and the heat conduction layer or the heat dissipation layer may be formed with an accommodation space configured to accommodate the anti-foaming layer. Heat conduction is not substantially performed through the anti-foaming layer, and the anti-foaming layer needs to consider anti-foaming characteristics without considering thermal conductivity thereof.

Furthermore, the accommodation space may include a bottom surface and a side wall connected to the bottom surface, and the anti-foaming layer may be provided with a top surface in contact with the bottom surface and an outer wall in contact with the side wall. Furthermore, the heat conduction layer may have a thickness of 5 μm to 50 μm.

Furthermore, the target may have a plate shape and have a central axis perpendicular to a surface of the plate, and along a same radial direction perpendicular to the central axis, a maximum distance from the active layer to the central axis is less than a maximum distance from the anti-foaming layer to the central axis, and the maximum distance from the anti-foaming layer to the central axis is less than a maximum distance from each of the heat conduction layer and the heat dissipation layer to the central axis.

Furthermore, the active layer, the heat conduction layer and the anti-foaming layer may be sequentially processed onto the heat dissipation layer by way of forming films.

Furthermore, material of the active layer may be Li, or a compound of Li, or an alloy of Li, and material of each of the heat conduction layer and the heat dissipation layer may be Cu, or a compound of Cu, or an alloy of Cu, and material of the anti-foaming layer may be Ta, or a compound of Ta, or an alloy of Ta. Furthermore, the active layer may have a thickness of 49 µm to 189 µm, and may be fully reacted with a proton beam having an energy of 2.2 MeV to 3 MeV, so that γ-ray pollution is reduced, energy deposition is not induced by excessive thickness, and heat dissipation performance of the target is not affected; the anti-foaming layer may be configured to suppress foaming induced by the charged particle beam and may have a thickness of 5 µm to 50 µm, so that hydrogen generated by the incident charged particle beam in the target may be rapidly diffused, concentration of hydrogen is weakened, or hydrogen is released to outside, foaming induced by the incident charged particle beam is effectively suppressed, thereby avoiding or reducing deformation of the target due to foaming, and prolonging service life of the target.

According to a fifth aspect of the disclosure, there is provided a substrate of a target for a device for generating a particle beam, the substrate includes an anti-foaming layer, a first heat dissipation layer and a second heat dissipation layer, the anti-foaming layer is capable of suppressing foaming of the target during generation of the particle beam, the first heat dissipation layer and the second heat dissipation layer transfer heat deposited in the target out, the anti-foaming layer is arranged between the first heat dissipation layer and the second heat dissipation layer, and the first heat dissipation layer is connected to the second heat dissipation layer.

Further, the first heat dissipation layer and the second heat dissipation layer may surround the anti-foaming layer, and the first heat dissipation layer or the second heat dissipation layer may be formed with an accommodation space configured to accommodate the anti-foaming layer. Furthermore, the accommodation space may include a bottom surface and a side wall connected to the bottom surface, and the anti-foaming layer may be provided with a top surface in contact with the bottom surface and an outer wall in contact with the side wall.

Further, the first heat dissipation layer and the anti-foaming layer may be sequentially processed onto the second heat dissipation layer by way of forming films.

Further, the target may have a plate shape and have a central axis perpendicular to a surface of the plate, and along a same radial direction perpendicular to the central axis, a maximum distance from the anti-foaming layer to the central axis is less than a maximum distance from each of the first heat dissipation layer and the second heat dissipation layer to the central axis.

Further, material of each of the first heat dissipation layer and the second heat dissipation layer may be Cu, or a compound of Cu, or an alloy of Cu, and material of the anti-foaming layer may be Ta, or a compound of Ta, or an alloy of Ta.

According to a sixth aspect of the disclosure, there is provided a neutron capture therapy system, including a neutron generation device and a beam shaping body. The neutron generation device includes an accelerator and a target, and a charged particle beam generated by acceleration of the accelerator acts with the target to generate a neutron beam. The beam shaping body includes a reflector, a moderator, a thermal neutron absorber, a radiation shield and a beam outlet. The moderator decelerates neutrons generated from the target to an epithermal neutron energy region. The reflector surrounds the moderator and guides deviated neutrons back to the moderator to improve intensity of an epithermal neutron beam. The thermal neutron absorber is configured to absorb thermal neutrons, to avoid excessive dose applied to normal tissues at shallow layers during treatment. The radiation shield is arranged around the beam outlet to shield leaked neutrons and photons, so as to reduce dose applied to normal tissues at non-irradiation regions. The target includes an active layer, an anti-foaming layer, a heat dissipation layer and a heat conduction layer, the active layer acts with the charged particle beam to generate the neutron beam, the anti-foaming layer is located behind the active layer in an incident direction of the charged particle beam and capable of suppressing foaming induced by the charged particle beam, the heat dissipation layer is located behind the anti-foaming layer in the incident direction of the charged particle beam and transfers heat deposited in the target out, and the heat conduction layer conducts heat of the active layer to the heat dissipation layer. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged.

Further, the heat conduction layer may be arranged between the active layer and the anti-foaming layer, and connected to the heat dissipation layer, so that the heat conduction layer has a large area contacting with the active layer and may rapidly conduct heat to the heat dissipation layer.

Further, the heat dissipation layer and the heat conduction layer may surround the anti-foaming layer, and the heat conduction layer is connected to the heat dissipation layer. Heat conduction is not substantially performed through the anti-foaming layer, and the anti-foaming layer needs to consider anti-foaming characteristics without considering thermal conductivity thereof. Furthermore, the heat dissipation layer or the heat conduction layer may be formed with an accommodation space configured to accommodate the anti-foaming layer. Furthermore, the accommodation space may include a bottom surface and a side wall connected to the bottom surface, and the anti-foaming layer may be provided with a top surface in contact with the bottom surface and an outer wall in contact with the side wall.

Further, the anti-foaming layer may be made of a material for suppressing foaming, such as a material with a hydrogen diffusion coefficient no less than 10 E−6 $cm^2$/s at 200° C. Furthermore, material of the anti-foaming layer may include at least one of Nb, Ta, Pd, V, an alloy thereof, or a compound thereof; each of the heat dissipation layer and the heat conduction layer is made of a heat conduction material. Furthermore, material of each of the heat dissipation layer and the heat conduction layer may include at least one of Cu, Fe, Al, an alloy thereof, or a compound thereof.

Further, the target may further include an anti-oxidation layer configured to prevent oxidation of the active layer and located in front of the active layer in the incident direction of the charged particle beam. The anti-oxidation layer enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam. Furthermore, material of the anti-oxidation layer may include at least one of Al, Ti, an alloy thereof, a compound thereof, or stainless steel.

Furthermore, the anti-oxidation layer, the active layer, the heat conduction layer, the anti-foaming layer and the heat dissipation layer may be sequentially arranged in the incident direction of the charged particle beam.

Furthermore, the active layer, the heat conduction layer and the anti-foaming layer may be sequentially processed onto the heat dissipation layer by way of forming films, and the anti-oxidation layer may be processed onto the active layer by way of forming a film, or the anti-oxidation layer may be a polymer film and processed onto the active layer by a film covering process. Furthermore, in a vacuum environment, materials of the anti-oxidation layer, the active layer, the heat conduction layer and the anti-foaming layer are sequentially evaporated into gases to be deposited in the heat dissipation layer, so that thickness of each layer of the target may be accurately controlled.

Furthermore, the target may have a plate shape and have a central axis perpendicular to a surface of the plate, and along a same radial direction perpendicular to the central axis, a maximum distance from the active layer to the central axis is less than a maximum distance from each of the anti-foaming layer and the anti-oxidation layer to the central axis, and the maximum distance from the anti-foaming layer to the central axis is less than a maximum distance from each of the heat dissipation layer and the heat conduction layer to the central axis.

Furthermore, material of the active layer may be Li, or a compound of Li, or an alloy of Li, the charged particle beam is a proton beam, and material of each of the heat dissipation layer and the heat conduction layer may be Cu, or a compound of Cu, or an alloy of Cu, and material of the anti-foaming layer may be Ta, or a compound of Ta, or an alloy of Ta, and material of the anti-oxidation layer may be Al or $Al_2O_3$ or polyimide.

Furthermore, the polyimide may have a molecular structural formula as follows:

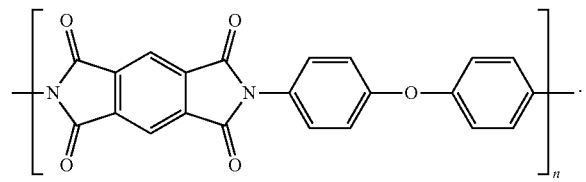

Furthermore, the proton beam may have an energy of 2.2 MeV to 3 MeV, the proton beam may generate a high cross-section acting with the lithium target, while excessive fast neutrons are not generated, to obtain a better beam quality. The active layer may have a thickness of 49 μm to 189 μm, and may be fully reacted with protons, so that γ-ray pollution is reduced, energy deposition is not induced by excessive thickness, and heat dissipation performance of the target is not affected; the anti-foaming layer may have a thickness of 5 μm to 50 μm, so that hydrogen generated by the incident charged particle beam in the target may be rapidly diffused, concentration of hydrogen is weakened, or hydrogen is released to outside, foaming induced by the incident charged particle beam is effectively suppressed, thereby avoiding or reducing deformation of the target due to foaming, and prolonging service life of the target; the anti-oxidation layer may have a thickness greater than 5 nm, the heat conduction layer may have a thickness of 5 μm to 50 μm, and service life of the target may be no less than 200 mA-h.

Further, the neutron capture therapy system may further include a treatment table and a collimator, the neutron beam generated by the neutron generation device passes through the beam shaping body and irradiates a patient on the treatment table, and a radiation shielding device is arranged between the patient and the beam outlet to shield radiation of a beam coming out of the beam outlet to the patient's normal tissues. The collimator is arranged at the rear of the beam outlet to converge the neutron beam, a first cooling pipe and a second cooling pipe are arranged in the beam shaping body, and the heat dissipation layer of the target is provided with a cooling inlet, a cooling outlet and a tortuous cooling channel arranged between the cooling inlet and the cooling outlet. An end of the first cooling pipe and an end of the second cooling pipe are connected to the cooling inlet and the cooling outlet of the target respectively, and another end of the first cooling pipe and another end of the second cooling pipe are connected to an external cooling source. A bending geometry of the tortuous cooling channel is a continuously curved smooth curve, or curved segments or straight segments sequentially connected end-to-end, and the continuously curved smooth curve is a sinusoidal wave function. The tortuous channel extends a circulation path, the circulation path may increase area of a heat transfer wall surface contacting with the cooling medium, thereby increasing heat dissipation surface, while forming a secondary flow, increasing stirring effect, improving heat transfer capability and heat dissipation effect, and helping to prolong service life of the target. The cooling channel uses a continuously curved smooth curve, such as a sinusoidal wave function, the continuously curved smooth curve may further reduce flow resistances induced by flow paths.

Furthermore, the target may be located in the beam shaping body, the accelerator is provided with an acceleration pipe to accelerate the charged particle beam, the acceleration pipe extends into the beam shaping body in the direction of the charged particle beam and sequentially passes through the reflector and the moderator, the target is arranged in the moderator and located at an end of the acceleration pipe, and the first cooling pipe and the second cooling pipe are arranged between the acceleration pipe and the reflector and the moderator.

According to a seventh aspect of the disclosure, there is provided a neutron capture therapy system, including a neutron generation device and a beam shaping body. The neutron generation device includes an accelerator and a target, and a charged particle beam generated by acceleration of the accelerator acts with the target to generate a neutron beam. The beam shaping body includes a reflector, a moderator, a thermal neutron absorber, a radiation shield and a beam outlet. The moderator decelerates neutrons generated from the target to an epithermal neutron energy region. The reflector surrounds the moderator and guides deviated neutrons back to the moderator to improve intensity of an epithermal neutron beam. The thermal neutron absorber is configured to absorb thermal neutrons, to avoid excessive dose applied to normal tissues at shallow layers during treatment. The radiation shield is arranged around the beam outlet to shield leaked neutrons and photons, so as to reduce dose applied to normal tissues at non-irradiation regions. The target includes an active layer, an anti-foaming layer and a heat dissipation layer, the active layer acts with the charged particle beam to generate the neutron beam, the anti-foaming layer is capable of suppressing foaming of the active layer during generation of the neutron beam, and the active layer has a thickness of 49 μm to 189 μm, and may be fully reacted with a proton beam, so that γ-ray pollution is reduced, energy deposition is not induced by excessive thickness, and heat dissipation performance of the target is not affected.

Further, the active layer may have a thickness of 97 μm.

Further, the target may further include a heat conduction layer arranged between the active layer and the anti-foaming layer, connected to the heat dissipation layer, and conducting heat of the active layer to the heat dissipation layer. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged. Furthermore, the heat conduction layer may have a thickness of 5 μm to 50 μm, the anti-foaming layer may have a thickness of 5 μm to 50 μm and may rapidly diffuse hydrogen generated by an incident charged particle beam in the target, so that concentration of hydrogen is weakened, or hydrogen is released to outside, foaming induced by the incident charged particle beam is effectively suppressed, thereby avoiding or reducing deformation of the target due to foaming, and prolonging service life of the target.

Further, material of the active layer may be Li, or a compound of Li, or an alloy of Li, and the charged particle beam may have an energy of 2.2 MeV to 3 MeV, the charged particle beam may generate a high cross-section acting with the lithium target, while excessive fast neutrons are not generated, to obtain a better beam quality.

Furthermore, material of each of the heat dissipation layer and the heat conduction layer may be Cu, or a compound of Cu, or an alloy of Cu, and material of the anti-foaming layer may be Ta, or a compound of Ta, or an alloy of Ta.

Furthermore, the active layer, the heat conduction layer and the anti-foaming layer may be sequentially processed onto the heat dissipation layer by way of forming films.

Furthermore, the target may have a plate shape and have a central axis perpendicular to a surface of the plate, and along a same radial direction perpendicular to the central axis, a maximum distance from the active layer to the central axis is less than a maximum distance from the anti-foaming layer to the central axis, and the maximum distance from the anti-foaming layer to the central axis is less than a maximum distance from each of the heat dissipation layer and the heat conduction layer to the central axis.

Further, the target may further include an anti-oxidation layer configured to isolate the active layer from air and have a thickness greater than 5 nm, the anti-oxidation layer enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam; the anti-oxidation layer may be made of $Al_2O_3$ or polyimide, and the anti-oxidation layer may be processed onto the active layer by way of forming a film, or the anti-oxidation layer may be a polymer film and processed onto the active layer by a film covering process.

According to an eighth aspect of the disclosure, there is provided a target for a device for generating a particle beam, the target sequentially includes an anti-oxidation layer, an active layer, an anti-foaming layer and a heat dissipation layer in an incident direction of a charged particle beam. The active layer acts with the charged particle beam to generate a neutron beam and has a thickness of 49 μm to 189 μm, and may be fully reacted with protons, so that γ-ray pollution is reduced, energy deposition is not induced by excessive thickness, and heat dissipation performance of the target is not affected; the anti-oxidation layer isolates the active layer from air and has a thickness greater than 5 nm, the anti-oxidation layer enables the target to be exposed to the air without technical storage, the anti-oxidation layer is very convenient especially when the target is installed and replaced, and the anti-oxidation layer may also prevent by-product of the active layer from overflowing the target, and material of the anti-oxidation layer is selected by considering that it is not easily corroded by the active layer and may reduce loss of an incident proton beam and heating induced by the proton beam; the anti-foaming layer is configured to suppress foaming induced by the charged particle beam and have a thickness of 5 μm to 50 μm, so that hydrogen generated by an incident charged particle beam in the target may be rapidly diffused, concentration of hydrogen is weakened, or hydrogen is released to outside, foaming induced by the incident charged particle beam is effectively suppressed, thereby avoiding or reducing deformation of the target due to foaming, and prolonging service life of the target.

Further, the charged particle beam may have an energy of 2.2 MeV to 3 MeV, the charged particle beam may generate a high cross-section acting with the lithium target, while excessive fast neutrons are not generated, to obtain a better beam quality.

Further, the target may further include a heat conduction layer conducting heat of the active layer to the heat dissipation layer and having a thickness of 5 μm to 50 μm. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged.

Furthermore, the anti-foaming layer may be arranged between the heat dissipation layer and the heat conduction layer, the heat conduction layer may be connected to the heat dissipation layer, and the heat dissipation layer or the heat conduction layer may be formed with an accommodation space configured to accommodate the anti-foaming layer. Heat conduction is not substantially performed through the anti-foaming layer, and the anti-foaming layer needs to consider anti-foaming characteristics without considering thermal conductivity thereof.

Furthermore, material of the active layer may be Li, or a compound of Li, or an alloy of Li, and material of each of the heat dissipation layer and the heat conduction layer may be Cu, or a compound of Cu, or an alloy of Cu, and material of the anti-foaming layer may be Ta, or a compound of Ta, or an alloy of Ta, and the anti-oxidation layer may be made of $Al_2O_3$ or polyimide.

Furthermore, the active layer, the heat conduction layer and the anti-foaming layer may be sequentially processed onto the heat dissipation layer by way of forming films, and the anti-oxidation layer may be processed onto the active layer by way of forming a film, or the anti-oxidation layer may be a polymer film and processed onto the active layer by a film covering process.

Furthermore, the target may have a plate shape and have a central axis perpendicular to a surface of the plate, and along a same radial direction perpendicular to the central axis, a maximum distance from the active layer to the central axis is less than a maximum distance from each of the anti-foaming layer and the anti-oxidation layer to the central axis, and the maximum distance from the anti-foaming layer to the central axis is less than a maximum distance from each of the heat dissipation layer and the heat conduction layer to the central axis.

According to a ninth aspect of the disclosure, there is provided a processing device of a target for a device for generating a particle beam, the target includes an active layer, an anti-foaming layer and a heat dissipation layer, the active layer is configured to generate the particle beam, the anti-foaming layer is capable of suppressing foaming of the active layer during generation of the particle beam, and the heat dissipation layer transfers heat deposited in the target out. The processing device includes a vacuum chamber, an exhaust device, an evaporation source, a bracket and a heating device, the exhaust device is configured to exhaust the vacuum chamber to form a vacuum environment; the evaporation source is configured to sequentially evaporate materials of the anti-foaming layer and the active layer into gases in the vacuum chamber; the bracket is configured to arrange the heat dissipation layer; and the heating device is configured to heat the heat dissipation layer, and materials of the gases are sequentially deposited in a surface of the heat dissipation layer facing toward the evaporation source. By using the processing device, thickness of each layer of the target may be accurately controlled.

Further, the target may further include an anti-oxidation layer configured to prevent oxidation of the active layer, and the evaporation source may evaporate the active layer into gas and evaporate the anti-oxidation layer into gas.

Further, the target may further include a heat conduction layer conducting heat of the active layer to the heat dissipation layer, and the evaporation source may evaporate the anti-foaming layer into gas, evaporate the heat conduction layer into gas, and evaporate the active layer into gas. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged.

Furthermore, the processing device may further include a film thickness detection device configured to detect thickness of each of the active layer and the anti-foaming layer and control deposition speeds of the gases.

According to a tenth aspect of the disclosure, there is provided a method of processing a target for a device for generating a particle beam, the target includes an active layer, an anti-foaming layer, a heat dissipation layer and a heat conduction layer, the active layer is configured to generate the particle beam, the anti-foaming layer is capable of suppressing foaming of the active layer during generation of the particle beam, the heat dissipation layer transfers heat deposited in the target out, and the heat conduction layer conducts heat of the active layer to the heat dissipation layer.

The method includes the following operations. The anti-foaming layer, the heat conduction layer and the active layer are sequentially processed onto the heat dissipation layer by way of forming films. Since the anti-foaming layer has poor heat dissipation performance and cannot effectively conduct heat deposited in the active layer to the heat dissipation layer, the heat conduction layer is arranged to directly and rapidly conduct heat deposited in the active layer to the heat dissipation layer, the heat is discharged on the heat dissipation layer through a cooling medium, so that temperature of the target is reduced, deformation of the target due to too high temperature is prevented, and service life of the target is prolonged; by using the method, thickness of each layer of the target may be accurately controlled.

Further, the target may further include an anti-oxidation layer configured to prevent oxidation of the active layer, and the method may include the following operations. The anti-oxidation layer with a film shape covers the active layer, or the anti-oxidation layer is processed onto the active layer by way of forming a film.

Further, the way of forming a film may be physical vapor deposition (PVD), sputtering, thermal welding, or atomic layer deposition (ALD).

According to an eleventh aspect of the disclosure, there is provided a method of processing a target for a device for generating a neutron beam, the target includes an anti-oxidation layer, an active layer, an anti-foaming layer and a heat dissipation layer, the active layer acts with a charged particle beam to generate the neutron beam, the anti-oxidation layer is located in front of the active layer in an incident direction of the charged particle beam and configured to prevent oxidation of the active layer, the anti-foaming layer is located behind the active layer in the incident direction of the charged particle beam and capable of suppressing foaming induced by the charged particle beam, and the heat dissipation layer is located behind the anti-foaming layer in the incident direction of the charged particle beam and transfers heat deposited in the target out. Method of processing the anti-oxidation layer is different from method of processing the active layer.

Further, the target may further include a heat conduction layer conducting heat of the active layer to the heat dissipation layer, and the anti-foaming layer, the heat conduction layer and the active layer may be sequentially processed onto the heat dissipation layer by way of forming films. Furthermore, in a vacuum environment, materials of the anti-foaming layer, the heat conduction layer and the active layer are sequentially evaporated into gases to be deposited in the heat dissipation layer, so that thickness of each layer of the target may be accurately controlled.

Further, the anti-oxidation layer may be a polymer film and processed onto the active layer by a film covering process. Furthermore, usage of the polymer film is convenient to be assembled and has low cost.

According to the neutron capture therapy system and the target for a device for generating a particle beam of the disclosure, the first heat dissipation layer is arranged to directly and rapidly conduct heat deposited in the active layer to the second heat dissipation layer, the heat is discharged on the second heat dissipation layer through a cooling medium, so that temperature of the target is reduced, deformation of the target due to too high temperature is prevented, and service life of the target is prolonged.

Further areas of applicability will become apparent from the description provided herein. It should be understood that the description and specific examples are intended for purposes of illustration only and are not intended to limit the scope of the disclosure.

BRIEF DESCRIPTION OF THE DRAWINGS

The accompanying drawings illustrate one or more embodiments of the disclosure and together with the written description, serve to explain the principles of the disclosure. Wherever possible, the same reference numbers are used throughout the drawings to refer to the same or like elements of an embodiment.

DETAILED DESCRIPTION OF THE DISCLOSURE

Embodiments of the disclosure will be further described in detail below with reference to the drawings, to enable those skilled in the art to implement the disclosure with reference to texts of the disclosure.

Figure 1:
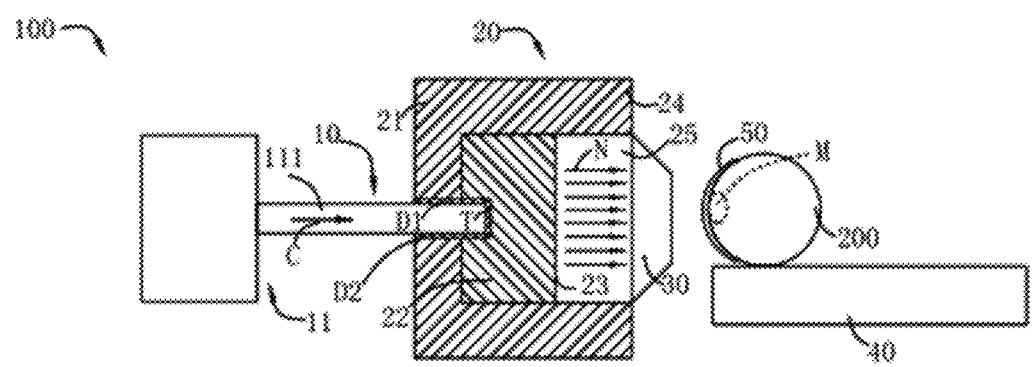
FIG. 1 is a schematic view of a neutron capture therapy system according to an embodiment of the disclosure.

As shown in FIG. 1, the neutron capture therapy system in the embodiment is further a BNCT system 100, and includes a neutron generation device 10, a beam shaping body 20, a collimator 30 and a treatment table 40. The neutron generation device 10 includes an accelerator 11 and a target T, the accelerator 111 accelerates charged particles (such as protons, deuterium cores, or the like) to generate a charged particle beam C such as a proton beam, the charged particle beam C irradiates to the target T and acts with the target T to generate a neutron beam N. Further, the target T is a metallic target. An appropriate nuclear reaction may be selected according to characteristics such as a desired neutron yield and energy, available energies of the accelerated charged particles, a current, physical and chemical properties of the metallic target, or the like. Nuclear reactions as commonly discussed include $^7Li(p, n)^7Be$ and $^9Be(p, n)^9B$, both of which are endothermic reactions and have energy thresholds of 1.881 MeV and 2.055 MeV respectively. An ideal neutron source for BNCT is an epithermal neutron at a keV energy level, theoretically, when protons with energies slightly higher than the threshold are used to bombard a metallic lithium target, neutrons with relatively low energies may be generated for clinical application without excessive deceleration process of neutrons. However, cross-sections of lithium (Li) and beryllium (Be) metallic targets acting with protons with threshold energies are not high, therefore protons with higher energies are usually selected to initiate a nuclear reaction, to generate a large enough neutron flux. An ideal target should have a high neutron yield, the generated neutron energy distribution is close to an epithermal neutron energy region (it will be described in detail below), there is not too much strong penetrating radiation, and there are characteristics such as safe, cheap, easy to operate, resistant to high temperature, or the like. However, nuclear reactions that meet most needs cannot be found actually. It is well known by those skilled in the art that the target T may also be made of an alloy of Li and Be, a compound of Li and Be, or other materials, for example, the target T may be formed by tantalum (Ta), or tungsten (W), an alloy of Ta and W, a compound of Ta and W, or the like. The accelerator 11 may be a linear accelerator, a cyclotron, a synchrotron, or a synchrocyclotron.

The neutron beam N generated by the neutron generation device 10 is irradiated to a patient 200 on the treatment table 40 by passing through the beam shaping body 20 and the collimator 30 sequentially. The beam shaping body 20 is capable of adjusting a beam quality of the neutron beam N generated by the neutron generation device 10, and the collimator 30 is configured to converge the neutron beam N, so that the neutron beam N has high targeting performance during treatment. The beam shaping body 20 further includes a reflector 21, a moderator 22, a thermal neutron absorber 23, a radiation shield 24 and a beam outlet 25. Neutrons generated by the neutron generation device 10 have large energy spectrums, contents of other kinds of neutrons and photons need to be reduced as much as possible, except epithermal neutrons meeting treatment needs, to avoid injuries to an operator or the patient. Therefore, neutrons coming out of the neutron generation device 10 need to pass through the moderator 22 to adjust energies (>40 keV) of fast neutrons therein to the epithermal neutron energy region (0.5 eV to 40 keV). The moderator 22 is made of a material having a large cross-section acting with the fast neutrons and a small cross-section acting with epithermal neutrons. In the embodiment, the moderator 22 is made of at least one of D2O, AlF3, Fluenal™, CaF2, Li2CO3, MgF2, or Al2O3. The reflector 21 surrounds the moderator 22, and reflects neutrons diffused around by passing through the moderator 22 back to the neutron beam N to improve utilization rate of neutrons, and is made of a material having a strong neutron reflection capability. In the embodiment, the reflector 21 is made of at least one of Pb or Ni, the thermal neutron (<0.5 eV) absorber 23 is arranged at the rear of the moderator 22 and made of a material having a large cross-section acting with thermal neutrons. In the embodiment, the thermal neutron absorber 23 is made of Li-6, and configured to absorb thermal neutrons passing through the moderator 22 to reduce contents of thermal neutrons in the neutron beam N, avoiding excessive dose applied to normal tissues at shallow layers during treatment. It may be understood that the thermal neutron absorber may also be integrated with the moderator, and material of the moderator contains Li-6. The radiation shield 24 is arranged around the beam outlet 25 and configured to shield neutrons and photons leaked from parts except the beam outlet 25, and material of the radiation shield 24 includes at least one of a photon shielding material or a neutron shielding material. In the embodiment, the material of the radiation shield 24 includes lead (Pb) used as the photon shielding material and polyethylene (PE) used as the neutron shielding material. It may be understood that the beam shaping body 20 may also have other configurations, as long as an epithermal neutron beam needed for treatment may be obtained. The collimator 30 is arranged at the rear of the beam outlet 25, and an epithermal neutron beam coming out of the collimator 30 is irradiated to the patient 200, and after passing through the normal tissues at shallow layers, the epithermal neutron beam is slowed down to thermal neutrons to reach a tumor cell M. It may be understood that the collimator 30 may also be cancelled or replaced by other structures, and the neutron beam comes out of the beam outlet 25 and is directly irradiated to the patient 200. In the embodiment, a radiation shielding device 50 is further arranged between the patient 200 and the beam outlet 25 to shield irradiation of a beam coming out of the beam outlet 125 to the patient's normal tissues, and it may be understood that the radiation shielding device 50 may not be provided.

After a boron (B-10)-containing drug is taken by or injected to the patient 200, the boron-containing drug is selectively aggregated in the tumor cell M, and two heavily charged particles 4He and 7Li are generated by using a characteristic of the boron (B-10)-containing drug having a high capture section for a thermal neutron, and through $^{10}B(n, \alpha)^7Li$ neutron capture and a nuclear fission reaction. The two charged particles have an average energy of about 2.33 MeV, and have characteristics of high linear energy transfer (LET) and short range. LET and range of α short particle are 150 keV/μm and 8 μm respectively, LET and range of the heavily charged particle 7Li are 175 keV/μm and 5 μm respectively, and the two particles have a total range approximately equivalent to a cell size, so that radiation injury to an organism may be limited to a cell level, and a purpose of locally killing tumor cells may be achieved on premise of not inducing too large injury to normal tissues.

Figure 2:
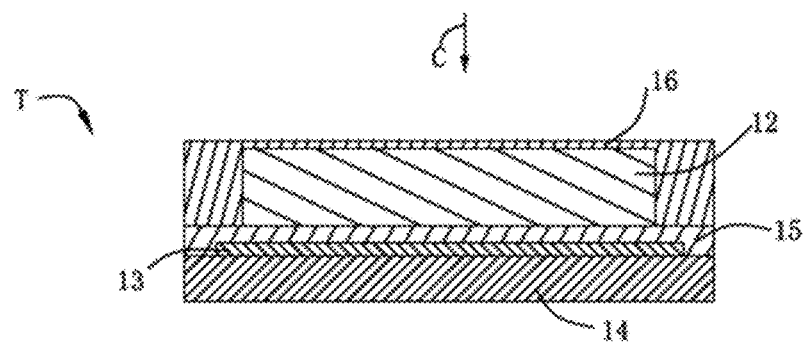
FIG. 2 is a schematic view of a target according to an embodiment of the disclosure.
Figure 3:
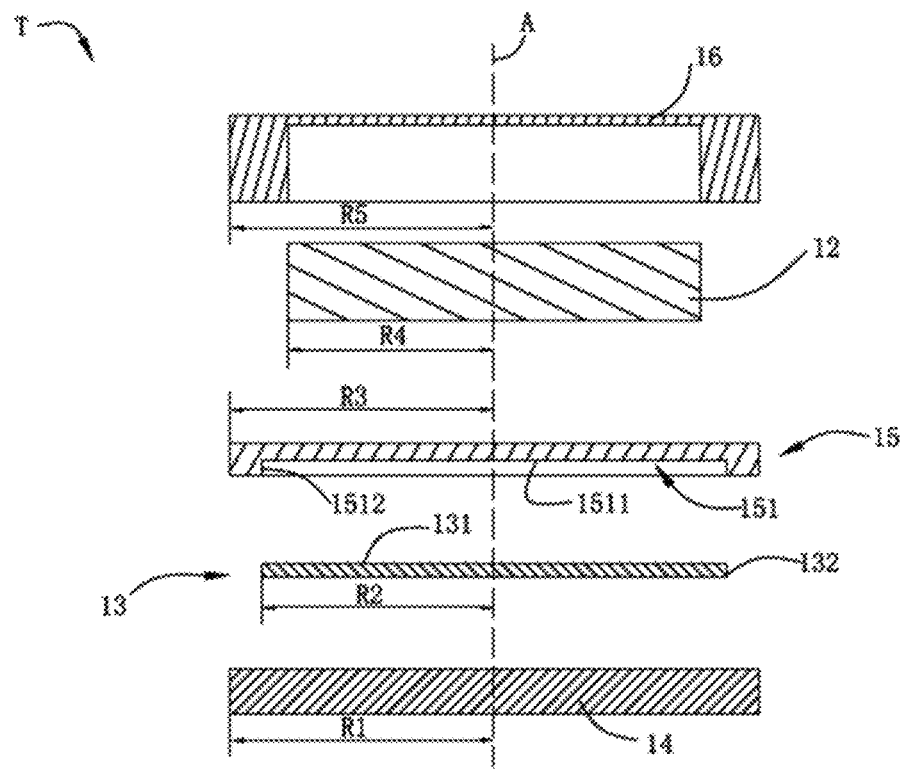
FIG. 3 is a schematic exploded view of the target of FIG. 2.

Structure of the target T is described in detail below with reference to FIG. 2 and FIG. 3.

The target T is arranged between the accelerator 11 and the beam shaping body 20, and the accelerator 11 is provided with an acceleration pipe 111 configured to accelerate the charged particle beam C. In the embodiment, the acceleration pipe 111 extends into the beam shaping body 20 in the direction of the charged particle beam C and sequentially passes through the reflector 21 and the moderator 22, the target T is arranged in the moderator 22 and located at an end of the acceleration pipe 111 to obtain a better neutron beam quality.

The target T includes an active layer 12, an anti-foaming layer 13, a (first) heat dissipation layer 14 and a (second heat dissipation layer) heat conduction layer 15. The active layer 12 acts with the charged particle beam C to generate a neutron beam, and during generation of neutrons, the target is subjected to irradiation of the accelerated charged particle beam C with a very high energy level, so that foaming of the target is induced, and temperature of the target increases, resulting in reduction in service life of the target. The anti-foaming layer 13 is located behind the active layer 12 in an incident direction of the charged particle beam C and is capable of rapidly diffusing hydrogen generated by an incident charged particle beam C in the target T, so that concentration of hydrogen is weakened, or hydrogen is released to outside, foaming induced by the incident charged particle beam C is effectively suppressed, thereby avoiding or reducing deformation of the target T due to foaming, and prolonging service life of the target. The anti-foaming layer 13 is made of a material for suppressing foaming, such as a material with a hydrogen diffusion coefficient no less than 10 E−6 cm$^2$/s at 200° C., and in an embodiment, material of the anti-foaming layer 13 includes at least one of Nb, Ta, Pd, V, an alloy thereof, or a compound thereof. The heat dissipation layer 14 is located behind the anti-foaming layer 13 in the incident direction of the charged particle beam C and transfers heat deposited in the target out, to be discharged through a cooling medium, so that temperature of the target is reduced, deformation of the target due to too high temperature is prevented, and service life of the target is prolonged. Since the anti-foaming layer 13 has poor heat dissipation performance and cannot effectively conduct heat deposited in the active layer 12 to the heat dissipation layer 14, the heat conduction layer 15 is arranged to directly and rapidly conduct heat deposited in the active layer 12 to the heat dissipation layer 14. Each of the heat dissipation layer 14 and the heat conduction layer 15 is made of a thermal conduction material, and in an embodiment, material of each of the heat dissipation layer 14 and the heat conduction layer 15 includes at least one of Cu, Fe, Al, an alloy thereof, or a compound thereof. The heat conduction layer 15 is arranged between the active layer 12 and the anti-foaming layer 13, and connected to the heat dissipation layer 14, that is, the anti-foaming layer 13 is arranged between the heat dissipation layer 14 and the heat conduction layer 15 connected to each other, such arrangement enables the heat conduction layer 15 to have a large area contacting with the active layer 12 and rapidly conduct heat to the heat dissipation layer 14. Heat conduction is not substantially performed through the anti-foaming layer 13, and the anti-foaming layer 13 needs to consider anti-foaming characteristics without considering thermal conductivity thereof. As shown in FIG. 3, in the embodiment, the heat dissipation layer 14 and the heat conduction layer 15 surround the anti-foaming layer 13, the heat conduction layer 15 is formed with an accommodation space 151 configured to accommodate the anti-foaming layer 13, the accommodation space 151 includes a bottom surface 1511 and a side wall 1512 connected to the bottom surface 1511, and the anti-foaming layer 13 is provided with a top surface 131 in contact with the bottom surface 1511 and an outer wall 132 in contact with the side wall 1512. It may be understood that the accommodation space may also be formed by the heat dissipation layer, or by the heat conduction layer and the heat dissipation layer together. The target T may further include an anti-oxidation layer 16 configured to prevent oxidation of the active layer 12 and located in front of the active layer 12 in the incident direction of the charged particle beam C, the anti-oxidation layer 16 and the heat conduction layer 15 enclose the active layer 12 together, that is, isolate the active layer 12 from air, to enable the target T to be exposed to the air without technical storage, the anti-oxidation layer 16 is very convenient especially when the target is installed and replaced, reducing cost significantly. The anti-oxidation layer 16 may also prevent by-product (such as 8Be) of the active layer 12 from overflowing the target T, and material of the anti-oxidation layer 16 is selected by considering that it is not easily corroded by the active layer and may reduce loss of an incident proton beam and heating induced by the proton beam, for example, material of the anti-oxidation layer 16 includes at least one of Al, Ti, an alloy thereof, a compound thereof, or stainless steel. In an embodiment, material of the anti-oxidation layer 16 uses Al2O3, since it has a better anti-oxidation effect through pre-oxidation, and radioactive products of Al activated by neutrons have short half-life periods, reducing secondary radiation. In another embodiment, the anti-oxidation layer 16 is a polymer film, such as a polyimide (PI) film, and polyimide has a molecular structure as follows:

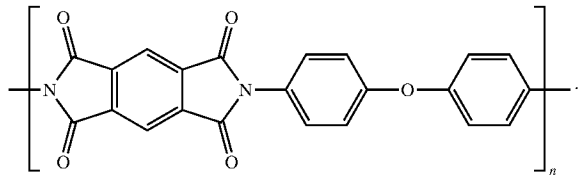

Polyimide is resistant to high temperature, and has high insulation performance, excellent mechanical performance and high irradiation-resistant performance, and has a thermal decomposition temperature reaching 400 degrees Celsius or above, may effectively shield high-energy neutrons, and may reduce radiation damage to normal tissues in case of deep tumors; and the polymer film is processed onto the active layer 12 by a film covering process (such as hot pressing, gluing, or the like), which is convenient to be assembled and has low cost. It may be understood that the anti-oxidation layer may not be provided.

In an embodiment, the proton beam is used to bombard the lithium target to generate neutrons, and the proton beam sequentially passes through the anti-oxidation layer 16, the active layer 12, the heat conduction layer 15, the anti-foaming layer 13 and the heat dissipation layer 14 in the incident direction. The proton beam has an energy of 2.2 MeV to 3 MeV, the proton beam may generate a high cross-section acting with the lithium target, while excessive fast neutrons are not generated, to obtain a better beam quality; the active layer 12 has a thickness of 49 µm to 189 µm, and may be fully reacted with protons, so that γ-ray pollution is reduced, energy deposition is not induced by excessive thickness, and heat dissipation performance of the target is not affected.

Figure 10:
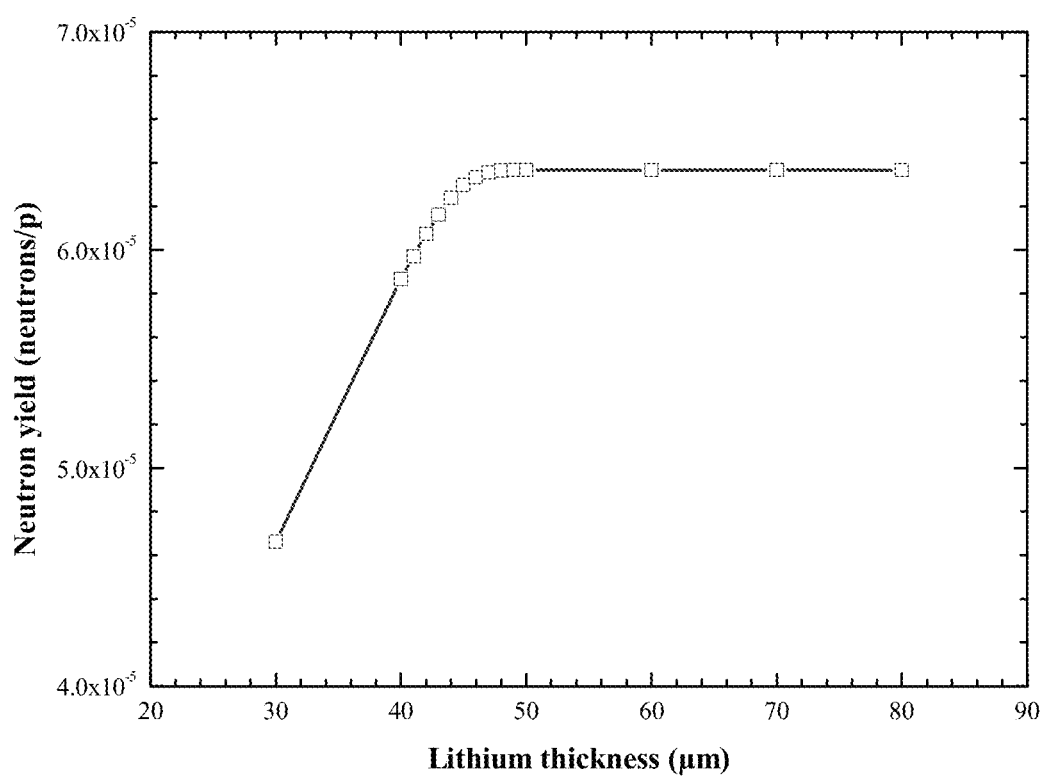
FIG. 10 is a neutron yield simulated and calculated by 2.2 MeV protons bombarding lithium (Li) targets with different thicknesses according to an embodiment of the disclosure.
Figure 11:
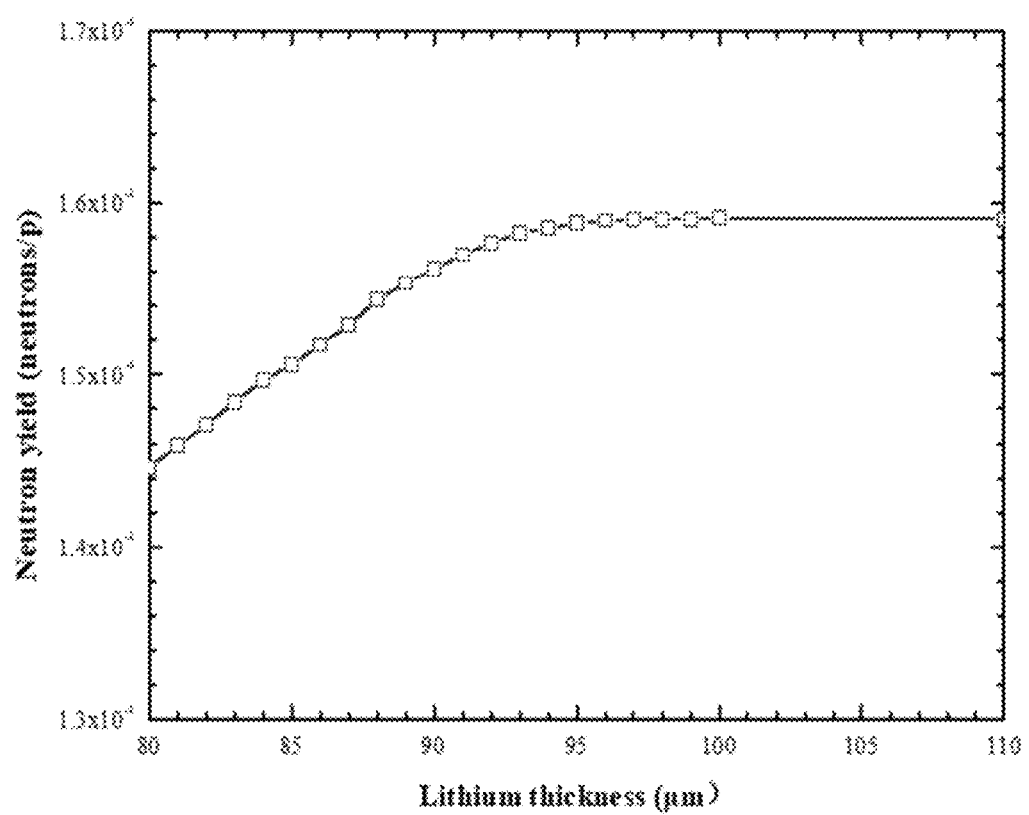
FIG. 11 is a neutron yield simulated and calculated by 2.5 MeV protons bombarding lithium (Li) targets with different thicknesses according to an embodiment of the disclosure.
Figure 12:
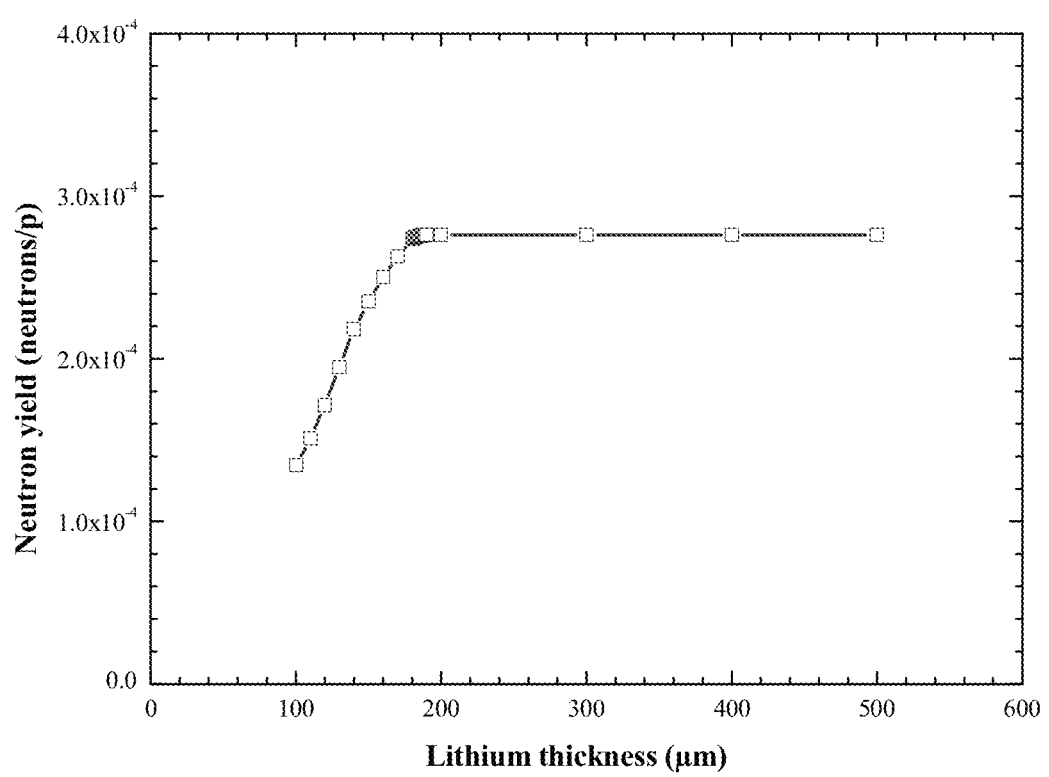
FIG. 12 is a neutron yield simulated and calculated by 3 MeV protons bombarding lithium (Li) targets with different thicknesses according to an embodiment of the disclosure.

A simulation software is used to simulate proton beams with energies of 2.2 MeV, 2.5 MeV and 3 MeV bombarding lithium targets with different thicknesses respectively, to obtain neutron yields in case of lithium targets with different thicknesses. As shown in FIG. 10 to FIG. 12, the neutron yield is the highest when the proton beam has an energy of 2.2 MeV, and the active layer of the target correspondingly has a thickness of 49 µm; the neutron yield is the highest when the proton beam has an energy of 2.5 MeV, and the active layer of the target correspondingly has a thickness of 97 µm; the neutron yield is the highest when the proton beam has an energy of 3 MeV, and the active layer of the target correspondingly has a thickness of 189 µm.

In the embodiment, the proton beam has an energy of 2.5 MeV, and the active layer 12 of the target has a thickness of 97 µm, the neutron beam needed for irradiation may be obtained, while the neutron yield is not too low.

Radioactive products are generated after Ta is activated by neutrons, thickness of the anti-foaming layer 13 should be as thin as possible on a premise of completely absorbing a residual proton beam, and the thickness of the anti-foaming layer 13 may be 5 µm to 50 µm. In order to reduce energy loss of the proton beam, thickness of the anti-oxidation layer 16 should be as thin as possible, and may be greater than 5 nm; the heat conduction layer 15 is made of Cu with ultra-high purity and has a thickness of 5 µm to 50 µm, to meet needs of rapidly conducting heat to the heat dissipation layer 14; and service life of the target is not less than 200 mA-h.

The target T has a plate shape as a whole and has a central axis A perpendicular to a surface of the plate. It may be understood that the thickness as described above is thickness of each layer of the target T along the central axis A of the target T, and thickness of an edge of each layer of the target T may be different according to structural needs.

Figure 4:
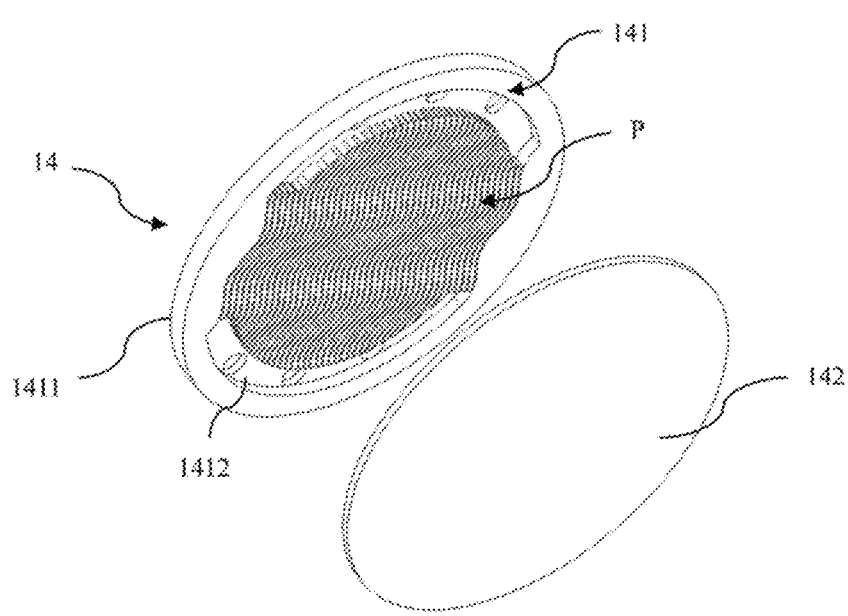
FIG. 4 is a schematic view of a first embodiment of a heat dissipation layer of the target of FIG. 2.
Figure 5:
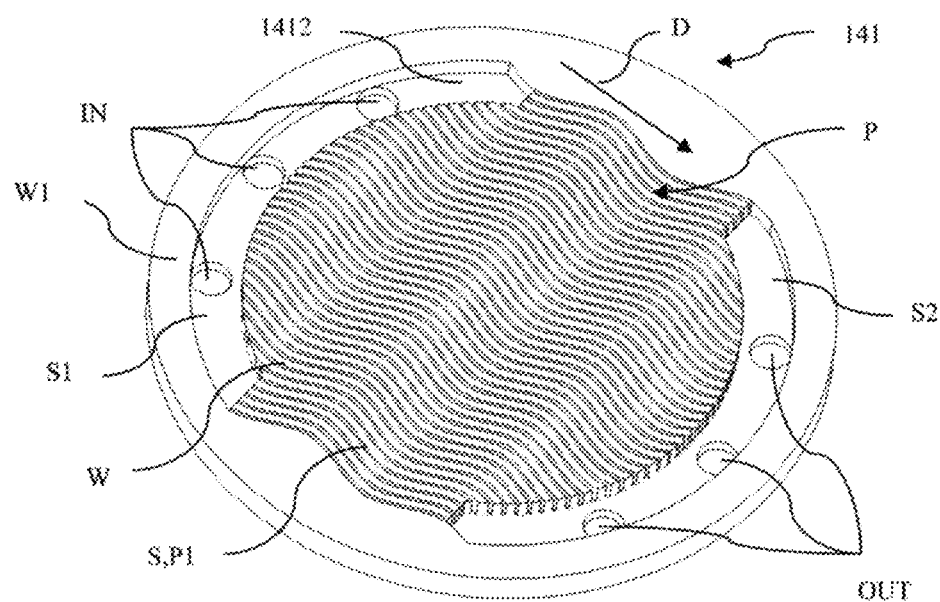
FIG. 5 is a schematic view of a first plate of the heat dissipation layer of FIG. 4.

The heat dissipation layer 14 may have a plurality of configurations, and thickness of the heat dissipation layer 14 may be selected to meet needs according to cooling structures. In a first embodiment of the heat dissipation layer shown in FIG. 4 and FIG. 5, the heat dissipation layer 14 has a plate shape and includes a first plate 141 and a second plate 142, the first plate 141 has a first side 1411 facing toward the active layer 12 and a second side 1412 opposite to the first side 1411, a cooling channel P for circulation of the cooling medium is formed on the second side 1412, and the second plate 142 is in close contact with the second side 1412 of the first plate 141. It may be understood that the cooling channel P may also be arranged on a side of the second plate 142 opposite to the first plate 141. The cooling channel P has a tortuous shape, the tortuous cooling channel P includes a plurality of parallel and tortuous sub-channels P1, that is, a plurality of tortuous walls W are arranged in parallel, and a tortuous groove S (i.e., the parallel and tortuous sub-channel P1) is formed between adjacent walls W. A bending geometry of the parallel and tortuous sub-channel P1 is a sinusoidal wave function:

$$k(x)\sin\left(\frac{x}{T}+\emptyset\right).$$

Here $\emptyset$ is a phase angle, x is a coordinate of a circulation direction (described in detail below) of the cooling medium, k is an amplitude, and T is a period.

It may be understood that the cooling channel P may also have another tortuous shape, such as a continuously curved smooth curve, or curved segments or straight segments sequentially connected end-to-end. The tortuous channel extends a circulation path, the circulation path may increase area of a heat transfer wall surface contacting with the cooling medium, thereby increasing heat dissipation surface, while forming a secondary flow, increasing stirring effect, improving heat transfer capability and heat dissipation effect, and helping to prolong service life of the target. The cooling channel P uses a continuously curved smooth curve, such as a sinusoidal wave function, the continuously curved smooth curve may further reduce flow resistances induced by flow paths. The tortuous cooling channel P may also have other arrangements.

The heat dissipation layer 14 also has a cooling inlet IN and a cooling outlet OUT, the cooling channel P is communicated with the cooling inlet IN and the cooling outlet OUT, and the cooling medium enters from the cooling inlet IN, passes through the cooling channel P, and comes out of the cooling outlet OUT. The target T is subjected to irradiation of the accelerated proton beam with a high energy level, temperature of the target increases, and the target generates heat. The heat conduction layer and the heat dissipation layer guide the heat out, and the heat is brought out through the cooling medium circulating in the cooling channel, to cool the target T. There are three cooling inlets IN and three cooling outlets OUT respectively, these cooling inlets and cooling outlets are symmetrically arranged at both ends of cooling channel P on the first plate 141, and extend and penetrate the first plate in a direction from the first side 1411 to the second side 1412. An inlet groove S1 and an outlet groove S2 are further formed on the second side 1412, and the inlet groove S1 and the outlet groove S2 are communicated with the cooling inlet IN, the cooling outlet OUT and each parallel and tortuous sub-channel P1 respectively, so that the cooling medium entering from the cooling inlet IN enters each parallel and tortuous sub-channel P1 from the inlet groove S1, and goes out from the cooling outlet OUT through the outlet groove S2. It may be understood that there may be other numbers or forms of cooling inlets IN and cooling outlets OUT, and the cooling inlet IN and the cooling outlet OUT may also be arranged on the second plate simultaneously or arranged on the first plate and the second plate respectively. A circumferential wall W1 is further arranged at peripheries of the cooling inlet IN and the cooling outlet OUT, the second plate 142 is in close contact with a surface of the circumferential wall W1 facing toward the second plate 142, and a cavity is formed between the first plate 141 and the second plate 142, so that the cooling medium entering from the cooling inlet IN may go out through the cooling outlet OUT, a surface of the second plate 142 in contact with the first plate 141 is a plane, and height of the tortuous wall W is the same as height of the circumferential wall W1. It may be understood that there may also be a stepped surface or another configuration. At this time, height of the tortuous wall W may be different from height of the circumferential wall W1, as long as each parallel and tortuous sub-channel P1 is independent of each other. Circulation directions D of the cooling medium in adjacent parallel and tortuous sub-channels P1 (an overall circulation direction of the cooling medium in the cooling channel) may also be different, further increasing heat dissipation efficiency. The inlet groove S1 and the outlet groove S2 may have other arrangements, for example, enabling the cooling medium to sequentially flow through each parallel and tortuous sub-channels P1. In the embodiment, material of each of the first plate and the second plate is Cu, Cu has good heat dissipation performance and low cost. The number and sizes of grooves S forming the cooling channel P are determined according to size of an actual target, and the groove may also have diverse cross-sectional shapes, such as a rectangle, a circle, a polygon, an ellipse, or the like, and different cross-sections may also have different shapes.

The first plate 141 and the second plate 142 are fixed together to the moderator 22 or an end of the acceleration pipe 111 by connection components such as bolts, screws, or the like, or by other fixing structures such as welding, or the like; or, the first plate 141 is connected to the second plate 142, and one of the first plate 141 and the second plate 142 is fixed into the moderator 22 or the end of the acceleration pipe 111. It may be understood that the heat dissipation layer may also be fixed or installed by using other detachable connections, to facilitate replacement of the target; the heat dissipation layer 14 may also be provided with a support member (not shown in the figures), at least the first plate 141 or the second plate 142 are fixed by the support member, and the cooling inlet IN and the cooling outlet OUT may also be arranged on the support member. In the embodiment, a first cooling pipe D1 and a second cooling pipe D2 are arranged between the acceleration pipe 111 and the reflector 21 and the moderator 22, an end of the first cooling pipe D1 and an end of the second cooling pipe D2 are connected to the cooling inlet IN and the cooling outlet OUT of the target T respectively, and another end of the first cooling pipe D1 and another end of the second cooling pipe D2 are connected to an external cooling source. The cooling medium may be deionized water, has an extremely low electrical conductivity, prevents current leakage generated in a high-voltage environment and prevents interference on generation of the neutron beam. It may be understood that the first cooling pipe and the second cooling pipe may also be arranged in the beam shaping body in other ways, and when the target is arranged outside the beam shaping body, the first cooling pipe and the second cooling pipe may be cancelled.

Figure 6:
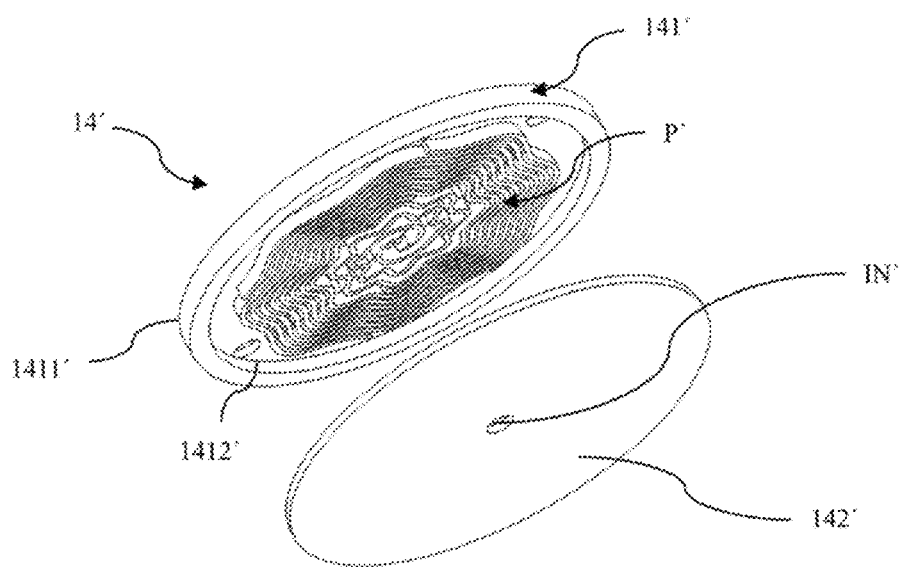
FIG. 6 is a schematic view of a second embodiment of a heat dissipation layer of the target of FIG. 2.
Figure 7:
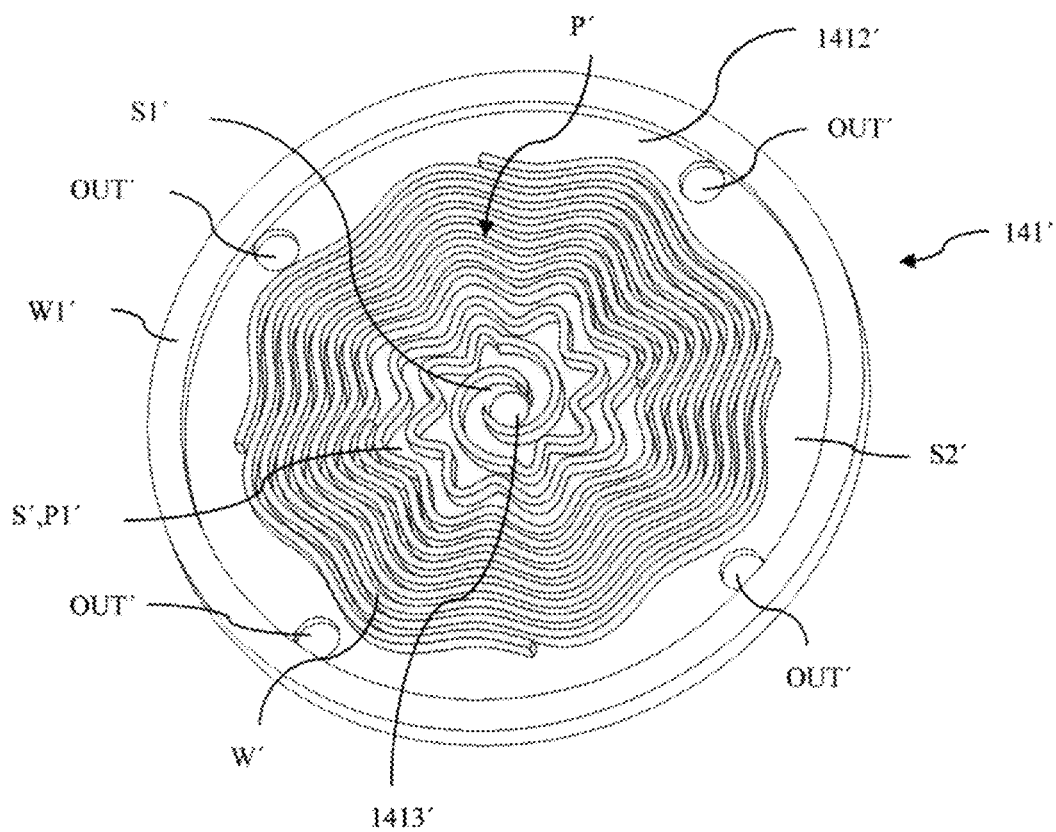
FIG. 7 is a schematic view of a first plate of the heat dissipation layer of FIG. 6.

As shown in FIG. 6 and FIG. 7, a second embodiment of the heat dissipation layer is shown, those of the second embodiment different from the first embodiment are described below. In the second embodiment of the heat dissipation layer, the tortuous cooling channel P' includes a plurality of helical and tortuous sub-channels P1', i.e., one or more tortuous walls W' are deployed in a helical line about the same center, each wall W' forms a plurality of layers in a radial direction, the layers formed by the walls W' are arranged interactively in the radial direction, and a slot S' (i.e., the helical and tortuous sub-channel P1') is formed between adjacent layers. A trajectory function of the helical and tortuous sub-channel P1' is:

$$R_{in} + (R_{out} - R_{in})\theta + K\theta\sin\left(\frac{\theta}{T}\right).$$

Here $R_{in}$ is a central radius, $R_{out}$ is an outer radius, $\theta$ is a polar coordinate angle, K is an amplitude, and T is a period.

A cooling inlet IN' is arranged at the center of a second plate 142' and communicated with the center of each helical and tortuous sub-channel P1'. There are four cooling outlets OUT' circumferentially and equally arranged at periphery of the cooling channel P' on a first plate 141', and extending and penetrating the first plate in a direction from a first side 1411' to a second side 1412'. It may be understood that other arrangements may also be provided. The center of the cooling channel P', i.e., the center of each helical and tortuous sub-channel P1', is used as an inlet groove S1', an outlet groove S2' is further formed on the second side 1412' of the first plate 141' and is communicated with the cooling outlet OUT' and each helical and tortuous sub-channel P1', so that the cooling medium entering from the cooling inlet IN' enters each helical and tortuous sub-channel P1' from the center of the cooling channel P', and goes out from the cooling outlet OUT' through the outlet groove S2'. A circumferential wall W1' is arranged at periphery of the cooling outlet OUT', the second plate 142' is in close contact with a surface of the circumferential wall W1' facing toward the second plate 142', and a cavity is formed between the first plate 141' and the second plate 142', so that the cooling medium entering from the cooling inlet IN' may go out through the cooling outlet OUT', a surface of the second plate 142' in contact with the first plate 141' is a plane, and height of the tortuous wall W' is the same as height of the circumferential wall W1'. It may be understood that there may also be a stepped surface or another configuration. At this time, height of the tortuous wall W' may be different from height of the circumferential wall W1', as long as each helical and tortuous sub-channel P1' is independent of each other. Circulation directions of the cooling medium in adjacent helical and tortuous sub-channels P1' may also be different, further increasing heat dissipation efficiency. A protrusion 1413' may also be arranged at the center of the first plate 141', to adjust flow, increase heat transfer area and reduce temperature of a central hot spot. Height of the protrusion 1413' may be higher than height of the wall W' and height of the circumferential wall W1', and extend into the cooling inlet IN' on the second plate; and the protrusion 1413' may have a shape of a solid cone, a hollow cone, a sheet, or the like.

Figure 8:
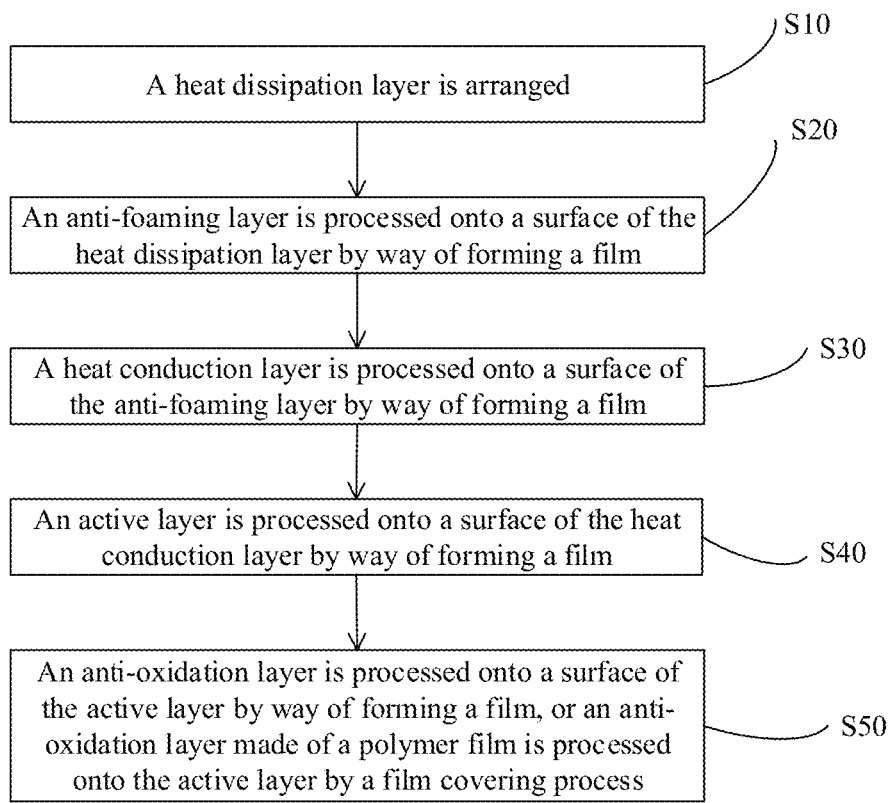
FIG. 8 is a schematic view of a target processing device according to an embodiment of the disclosure.

In order to achieve configuration of the above target, the target T may use a process of processing other layers (the anti-oxidation layer 16, the active layer 12, the heat conduction layer 15 and the anti-foaming layer 13) onto the heat dissipation layer 14 by way of forming films, for example, by PVD, sputtering, thermal welding, ALD, or the like. As shown in FIG. 8, a process of manufacturing the target T includes operations as follows.

In operation S10, a heat dissipation layer 14 (configured as a copper plate) is arranged, and a maximum distance from the heat dissipation layer 14 to a central axis A of the target T is R1.

In operation S20, an anti-foaming layer 13 (Ta) is processed onto a surface of the heat dissipation layer 14 by way of forming a film, for example, by sputtering, and a maximum distance from the anti-foaming layer 13 to the central axis A is R2, R2 is less than R1. An area of the heat dissipation layer 14 where formation of the film (the anti-foaming layer 13) is not needed, needs to be shielded, for example, a metal plate is used to shield the area, and a distance from a surface of the heat dissipation layer 14 to the central axis A is in an interval of R2-R1.

In operation S30, a heat conduction layer 15 (Cu) is processed onto a surface of the anti-foaming layer 13 by way of forming a film, for example, by sputtering, and a maximum distance from the heat conduction layer 15 to the central axis A is R3, R3 is greater than R2. That is, the metal plate used for shielding in operation S31 needs to be removed before operation S32 is performed.

In operation S40, an active layer 12 (Li) is processed onto a surface of the heat conduction layer 15 by way of forming a film, for example, by thermal welding or PVD, and a maximum distance from the active layer 12 to the central axis A is R4, R4 is less than R3. An area of a surface of a workpiece obtained in operation S32 where formation of the film (the active layer 12) is not needed, needs to be shielded, for example, a metal plate is used to shield the area, and a distance from the surface of the workpiece obtained in operation S32 to the central axis A is in an interval of R4-R3. In the embodiment, R4 is less than R2, so that the anti-foaming layer may completely absorb residual protons.

In operation S50, an anti-oxidation layer 16 (Al2O3) is processed onto a surface of the active layer 12 by way of forming a film, for example, by ALD, and a maximum distance from the anti-oxidation layer 16 to the central axis A is R5, R5 is greater than R4. That is, the metal plate used for shielding in operation S33 needs to be removed before operation S34 is performed.

In the embodiment, each of R5 and R3 is equal to R1, and it may be understood that other arrangements may also be provided.

When the anti-oxidation layer 16 is a polymer film (such as a PI film), operation S50 may also implemented by processing the anti-oxidation layer 16 made of the polymer film onto the active layer 12 by a film covering process, for example, by hot pressing and gluing processes. An organic silicon pressure-sensitive adhesive without containing moisture may be used, which does not react with metal layers, and is convenient to be assembled and has low cost. Furthermore, a liquid polymer film material may be coated on the active layer 12 and cured (which may also be considered as processing by way of forming a film), for example, by rotary coating, which is more uniform.

Figure 9:
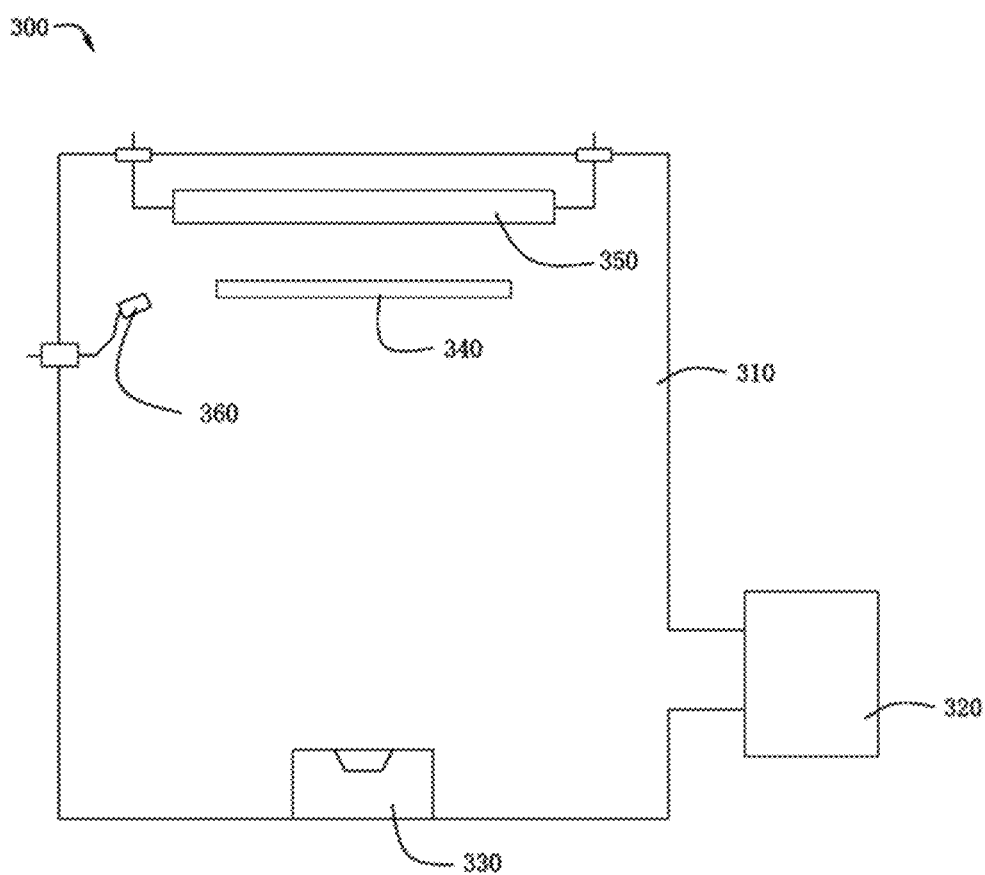
FIG. 9 is a flowchart of a target method according to an embodiment of the disclosure.

In an embodiment, the target T may use a process of sequentially forming materials of layers (the anti-oxidation layer 16, the active layer 12, the heat conduction layer 15 and the anti-foaming layer 13) into gases in a vacuum environment, to be deposited in the heat dissipation layer 14 (PVD). As shown in FIG. 9, in the embodiment, a processing device 300 of the target T includes a vacuum chamber 310, an exhaust device 320, an evaporation source 330, a bracket 340 and a heating device 350. The exhaust device 320 is configured to exhaust the vacuum chamber 310 to form a vacuum environment. The evaporation source 330 is configured to sequentially evaporate materials of the layers into gases in the vacuum chamber 310, and in the embodiment, the evaporation source 330 is an electron beam or ion beam evaporation and is arranged at the bottom of the vacuum chamber. The bracket 340 is configured to arrange the heat dissipation layer 14, and in the embodiment, the bracket 340 is arranged at the top of the vacuum chamber 310. The heating device 350 is configured to heat the heat dissipation layer 14, and materials of the gases are deposited in a surface of the heat dissipation layer 14 facing toward the evaporation source 330. The processing device 300 may also include a film thickness detection device 360 configured to detect thickness of each layer of material and control deposition speeds of the gases.

By using the above processing device and processes, thickness of each layer of the target may be accurately controlled. The bracket 340 may also have a rotary structure where a plurality of heat dissipation layers are fixed and sequentially processed to form films, improving processing efficiency; and a plurality of targets may also be processed simultaneously. It may be understood that the processing device 300 may also have other configurations.

According to the target of the embodiment, due to the structure and processing processes thereof, the target has better anti-foaming and heat dissipation performance, and has service life no less than 400 mA-h. It may be understood that the processing device and the method of the embodiment may also be applied to a target without an anti-oxidation layer or a heat conduction layer, and the target T may also use other manufacturing methods.

In the embodiment, the target T has a circular plate shape as a whole. It may be understood that the target T may also have a rectangular plate shape or other plate shapes; the target T may also have other solid shapes; and the target T may also be movable relative to the accelerator or the beam shaping body, so as to facilitate replacement of the target or enable the particle beam to uniformly act with the target. The anti-foaming layer 13, the heat dissipation layer 14 and the heat conduction layer 15 may also form a substrate T1 of the target T, where different active layers 12 are processed to form different targets T. The target T may further include a support portion (not shown) configured to support or install the target, the support portion may also be configured to install at least a part of the first cooling pipe D1 and the second cooling pipe D2, and the support portion may be made of an Al alloy material, radioactive products of Al activated by neutrons have short half-life periods, reducing secondary radiation.

It may be understood that the target of the disclosure may also be applied to neutron generation devices in other medical and non-medical fields, as long as generation of neutrons is based on a nuclear reaction between a particle beam and the target, the target is also made of different materials based on different nuclear reactions; and the target may also be applied to other particle beam generation devices.

While the illustrative specific implementations of the invention have been described as above, so that those skilled in the art understand the invention, it should be apparent that the invention is not limited to the scope of the specific implementations, various changes are apparent for those of ordinary skill in the art and fall within the scope of protection of the invention, as long as these changes fall within the spirit and scope of the invention as described and determined by the appended claims.

What is claimed is:

1. A neutron capture therapy system, comprising:
a neutron generation device and a beam shaping body, wherein the neutron generation device comprises an accelerator and a target, and a charged particle beam generated by acceleration of the accelerator acts with the target to generate a neutron beam, the beam shaping body comprises a reflector, a moderator, a thermal neutron absorber, a radiation shield and a beam outlet, the moderator decelerates neutrons generated from the target to an epithermal neutron energy region, the reflector surrounds the moderator and guides deviated neutrons back to the moderator to improve intensity of an epithermal neutron beam, the thermal neutron absorber is configured to absorb thermal neutrons, to avoid excessive dose applied to normal tissues at shallow layers during treatment, the radiation shield is arranged around the beam outlet to shield leaked neutrons and photons, so as to reduce dose applied to normal tissues at non-irradiation regions, characterized in that the target comprises an active layer, an anti-foaming layer, a heat conduction layer and a heat dissipation layer, the active layer acts with an incident charged particle beam to generate a neutron beam, the anti-foaming layer is located behind the active layer in an incident direction of the charged particle beam and capable of suppressing foaming of the active layer during generation of the particle beam, the heat conduction layer transfers heat deposited in the active layer to the heat dissipation layer, and the heat dissipation layer discharges the heat;
wherein the heat conduction layer is arranged between the active layer and the anti-foaming layer, and the heat conduction layer is directly connected to the heat dissipation layer.

2. The neutron capture therapy system of claim 1, wherein the heat conduction layer and the heat dissipation layer surround the anti-foaming layer, and the heat conduction layer or the heat dissipation layer is formed with an accommodation space configured to accommodate the anti-foaming layer.

3. The neutron capture therapy system of claim 2, wherein the accommodation space comprises a bottom surface and a side wall connected to the bottom surface, and the anti-foaming layer is provided with a top surface in contact with the bottom surface and an outer wall in contact with the side wall.

4. The neutron capture therapy system of claim 1, wherein material of the active layer is Li, or a compound of Li, or an alloy of Li.

5. The neutron capture therapy system of claim 1, wherein the charged particle beam has an energy of 2.2 MeV to 3 MeV.

6. The neutron capture therapy system of claim 1, wherein the active layer has a thickness of 49 μm to 189 μm.

7. The neutron capture therapy system of claim 1, wherein material of the anti-foaming layer comprises at least one of Nb, Ta, Pd, V, an alloy thereof, or a compound thereof.

8. The neutron capture therapy system of claim 1, wherein material of each of the heat conduction layer and the heat dissipation layer comprises at least one of Cu, Fe, Al, an alloy thereof, or a compound thereof.

9. The neutron capture therapy system of claim 1, further comprising an anti-oxidation layer configured to prevent oxidation of the active layer, and the anti-oxidation layer, the active layer, the heat conduction layer, the anti-foaming layer and the heat dissipation layer sequentially arranged in the incident direction of the charged particle beam.

10. The neutron capture therapy system of claim 9, having a plate shape and having a central axis perpendicular to a surface of the plate, and along a same radial direction perpendicular to the central axis, a maximum distance from the active layer to the central axis less than a maximum distance from each of the anti-foaming layer and the anti-oxidation layer to the central axis, and the maximum distance from the anti-foaming layer to the central axis less than a maximum distance from each of the heat conduction layer and the heat dissipation layer to the central axis.

11. The neutron capture therapy system of claim 9, wherein the anti-foaming layer has a thickness of 5 μm to 50 μm, each of the heat conduction layer and the heat dissipation layer has a thickness of 5 μm to 50 μm, and the anti-oxidation layer has a thickness greater than 5 nm.

12. The neutron capture therapy system of claim 9, wherein material of the anti-oxidation layer comprises at least one of Al, Ti, an alloy thereof, a compound thereof, or stainless steel.

13. The neutron capture therapy system of claim 12, wherein the anti-oxidation layer, the active layer, the heat conduction layer and the anti-foaming layer are sequentially processed onto the heat dissipation layer by way of forming films.

14. The neutron capture therapy system of claim 9, wherein the anti-oxidation layer is a polymer film and processed onto the active layer by a film covering process.

15. The neutron capture therapy system of claim 14, wherein the polymer film is polyimide with a molecular structure as follows:

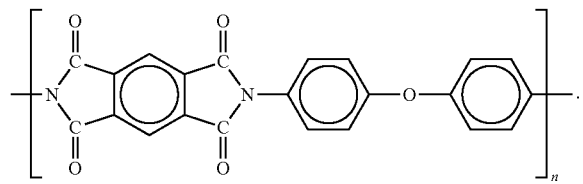

16. The neutron capture therapy system of claim 1, further comprising: a treatment table and a collimator, the neutron beam generated by the neutron generation device passes through the beam shaping body and irradiates a patient on the treatment table, and a radiation shielding device is arranged between the patient and the beam outlet to shield radiation of a beam coming out of the beam outlet to the patient's normal tissues, the collimator is arranged at the rear of the beam outlet to converge the neutron beam, a first cooling pipe and a second cooling pipe are arranged in the beam shaping body, and the heat dissipation layer of the target is provided with a cooling inlet, a cooling outlet and a tortuous cooling channel arranged between the cooling inlet and the cooling outlet.

17. The neutron capture therapy system of claim 16, wherein an end of the first cooling pipe and an end of the second cooling pipe are connected to the cooling inlet and the cooling outlet of the target respectively, and another end of the first cooling pipe and another end of the second cooling pipe are connected to an external cooling source.

18. The neutron capture therapy system of claim 17, wherein a bending geometry of the tortuous cooling channel is a continuously curved smooth curve, or curved segments or straight segments sequentially connected end-to-end, and the continuously curved smooth curve is a sinusoidal wave function.

19. The neutron capture therapy system of claim 16, wherein the target is located in the beam shaping body, the accelerator is provided with an acceleration pipe to accelerate the charged particle beam, the acceleration pipe extends into the beam shaping body in the direction of the charged particle beam and sequentially passes through the reflector and the moderator, the target is arranged in the moderator and located at an end of the acceleration pipe, and the first cooling pipe and the second cooling pipe are arranged between the acceleration pipe and the reflector and the moderator.

* * * * *